United States Patent
Gunderson et al.

(10) Patent No.: US 11,883,061 B2
(45) Date of Patent: Jan. 30, 2024

(54) CUTTING BALLOON CATHETER WITH FLEXIBLE CUTTING BLADES

(71) Applicant: BOSTON SCIENTIFIC SCIMED, INC., Maple Grove, MN (US)

(72) Inventors: Richard Gunderson, St. Paul, MN (US); Joseph Zielinski, Plymouth, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 348 days.

(21) Appl. No.: 17/306,497

(22) Filed: May 3, 2021

(65) Prior Publication Data
US 2021/0251652 A1    Aug. 19, 2021

Related U.S. Application Data

(63) Continuation of application No. 16/048,548, filed on Jul. 30, 2018, now Pat. No. 11,020,142, which is a
(Continued)

(51) Int. Cl.
*A61B 17/3207* (2006.01)
*A61M 25/10* (2013.01)
(Continued)

(52) U.S. Cl.
CPC .. *A61B 17/320725* (2013.01); *A61B 17/3439* (2013.01); *A61M 25/104* (2013.01);
(Continued)

(58) Field of Classification Search
CPC ............. A61M 25/10; A61M 25/1002; A61M 25/1011; A61M 25/104; A61M 2025/1004; A61M 2025/107; A61M 2025/109; A61M 2025/1079; A61M 2025/1086; A61M 2025/1093; A61B 17/32; A61B 17/32075; A61B 17/320016; A61B 17/320725; A61B 17/3439; A61B 2017/2205; A61B 2017/22061; A61B 2017/320004; A61B 2017/320008; A61F 2/915; A61F 2002/91508; A61F 2002/91516; A61F 2002/91525; A61F 2002/91533; A61F 2002/91541; A61F 2002/9155;
(Continued)

(56) References Cited

U.S. PATENT DOCUMENTS 6,500,186 B2   12/2002   Afontaine et al.
6,562,062 B2   5/2003    Jenusaitis et al.
(Continued)

FOREIGN PATENT DOCUMENTS

GB     2487400 A   *  7/2012   ..... A61B 17/320725

*Primary Examiner* — Kankindi Rwego
(74) *Attorney, Agent, or Firm* — Seager, Tufte & Wickhem LLP

(57) ABSTRACT

A cutting balloon catheter including a balloon mounted on a distal portion of a catheter shaft. The balloon includes a cutting member mounted on an exterior surface of the balloon which includes one or more features for providing the cutting member with enhanced flexibility for navigating tortuous anatomy and more closely conforms to the expansion characteristics of the balloon to which the cutting member is mounted.

9 Claims, 13 Drawing Sheets

Related U.S. Application Data continuation of application No. 14/955,519, filed on Dec. 1, 2015, now Pat. No. 10,058,349, which is a continuation of application No. 13/548,577, filed on Jul. 13, 2012, now Pat. No. 9,226,768.

(60) Provisional application No. 61/508,126, filed on Jul. 15, 2011.

(51) Int. Cl.
 *A61B 17/22* (2006.01)
 *A61B 17/34* (2006.01)

(52) U.S. Cl.
 CPC .............. *A61B 2017/22061* (2013.01); *A61M 2025/109* (2013.01); *A61M 2025/1086* (2013.01)

(58) Field of Classification Search
 CPC .. A61F 2002/91558; A61F 2002/91566; A61F 2002/91575; A61F 2002/91583; A61F 2002/91591
 USPC ....... 606/167, 168, 169, 170, 171, 180, 191, 606/192, 194; 604/93.01, 96.01, 103.06
 See application file for complete search history.

(56) References Cited

U.S. PATENT DOCUMENTS

| | | |
|---|---|---|
| 6,632,231 B2 | 10/2003 | Radisch, Jr. |
| 7,172,609 B2 | 2/2007 | Radisch, Jr. |
| 7,291,158 B2 | 11/2007 | Crow et al. |
| 7,662,163 B2 | 2/2010 | Grayzel et al. |
| 7,691,116 B2 | 4/2010 | Goodin et al. |
| 7,754,047 B2 | 7/2010 | Kelley |
| 8,043,311 B2 | 10/2011 | Radisch, Jr. et al. |
| 9,226,768 B2 | 1/2016 | Gunderson et al. |
| 10,058,349 B2 | 8/2018 | Gunderson et al. |
| 2003/0040770 A1 | 2/2003 | Radisch, Jr. |
| 2005/0102020 A1* | 5/2005 | Grayzel .................. A61F 2/958 623/1.11 |
| 2005/0149102 A1 | 7/2005 | Radisch, Jr. |
| 2005/0228343 A1* | 10/2005 | Kelley ........... A61B 17/320725 29/428 |
| 2005/0240148 A1 | 10/2005 | Cheves et al. |
| 2006/0106412 A1 | 5/2006 | Crow et al. |
| 2006/0106413 A1 | 5/2006 | Bence et al. |
| 2006/0111736 A1 | 5/2006 | Kelley |
| 2006/0184191 A1 | 8/2006 | O'Brien |
| 2012/0191111 A1* | 7/2012 | Aggerholm .... A61B 17/320725 606/159 |

* cited by examiner

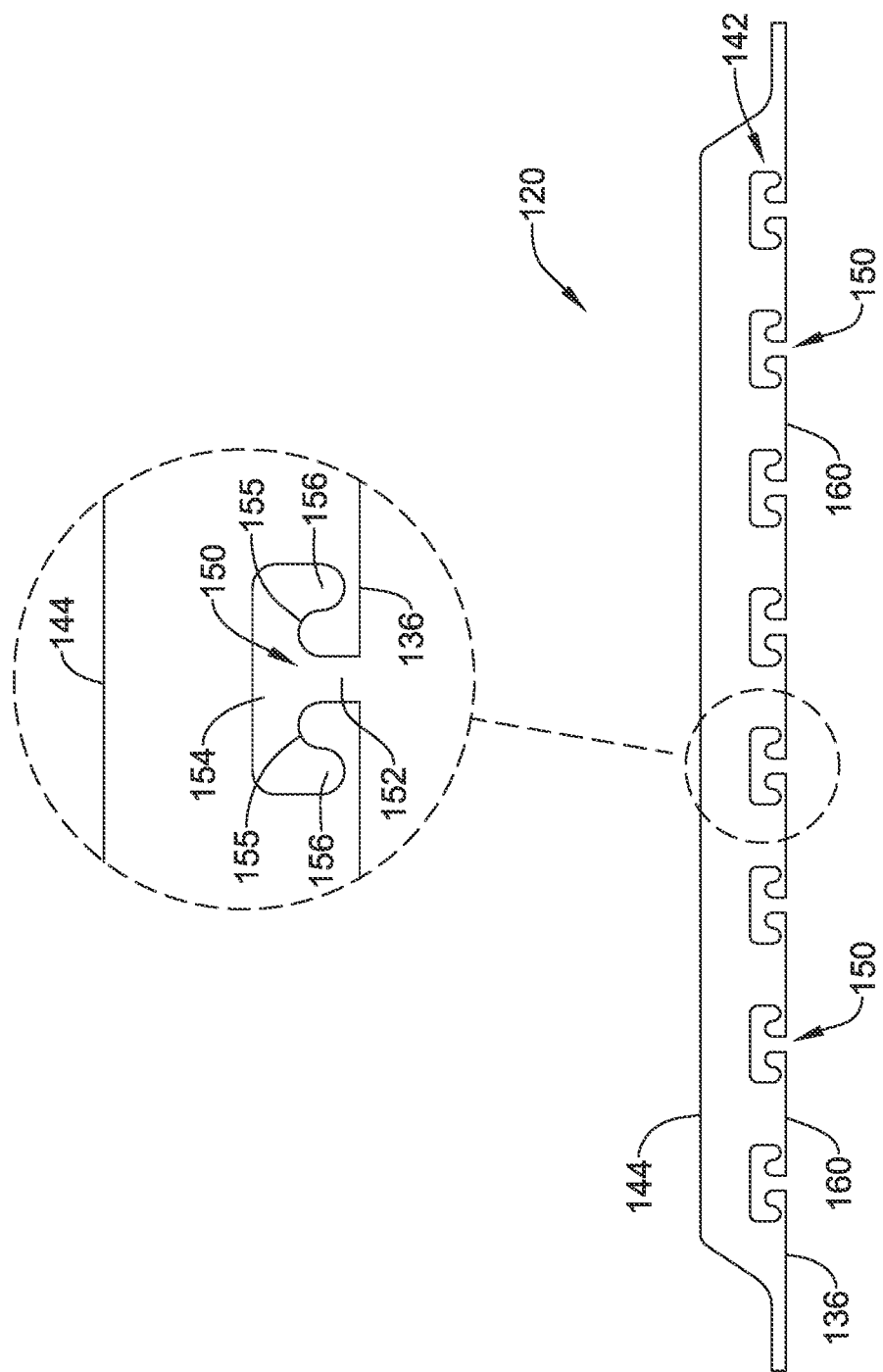

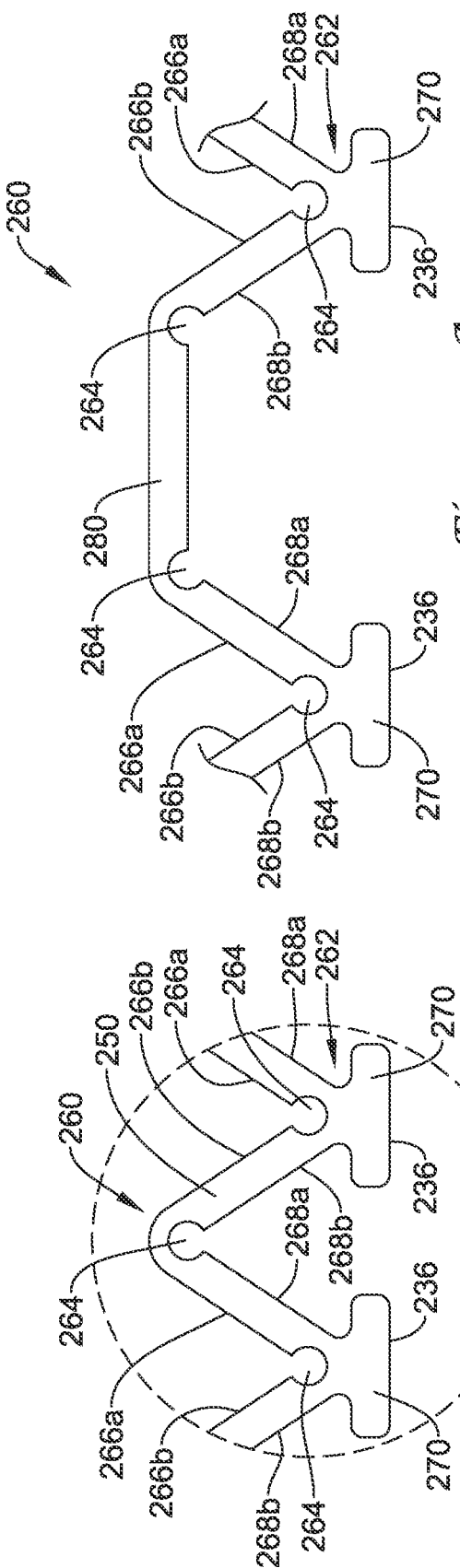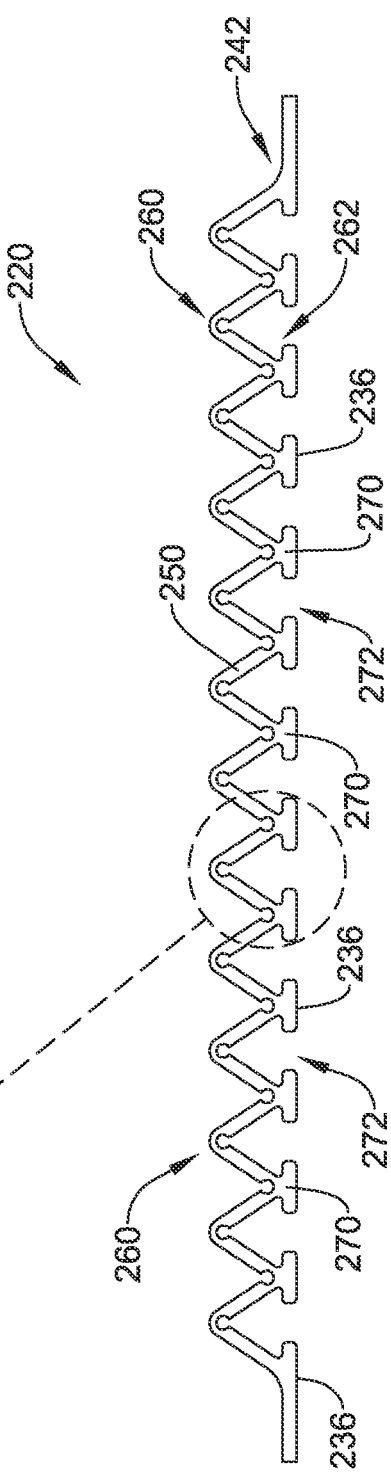

CUTTING BALLOON CATHETER WITH FLEXIBLE CUTTING BLADES

CROSS-REFERENCE TO RELATED APPLICATIONS

This application is a continuation of U.S. patent application Ser. No. 16/048,548, filed on Jul. 30, 2018, which is a continuation of U.S. patent application Ser. No. 14/955,519, filed on Dec. 1, 2015, now U.S. Pat. No. 10,058,349, which is a continuation of U.S. patent application Ser. No. 13/548,577, filed on Jul. 13, 2012, now U.S. Pat. No. 9,226,768 and claims benefit of 61/508,126, filed on Jul. 15, 2011, the contents of which are fully incorporated herein by reference.

TECHNICAL FIELD

The disclosure is directed to angioplasty balloon catheters including one or more cutting blades mounted to the balloon. More particularly, the disclosure is directed to cutting blades of a cutting balloon catheter having enhanced flexibility characteristics.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action, or lack of oxygenation and/or circulation to other regions of the body.

Occluded, stenotic, or narrowed blood vessels, as well as native or synthetic arteriovenous dialysis fistulae, may be treated in a recanalization procedure, such as with an angioplasty balloon catheter advanced over a guidewire to an occlusion so that the balloon is positioned across the occlusion. The balloon is then inflated to enlarge the passageway through the occlusion.

One of the major obstacles in treating coronary artery disease and/or treating blocked blood vessels or fistulae is re-stenosis or re-narrowing of the passageway through the occlusion subsequent to an angioplasty procedure or other recanalization procedure. Evidence has shown that cutting or scoring the stenosis, for example, with an angioplasty balloon equipped with a cutting element, during treatment can reduce incidence of re-stenosis. Additionally, cutting or scoring the stenosis may reduce trauma at the treatment site and/or may reduce the trauma to adjacent healthy tissue. Cutting elements may also be beneficial additions to angioplasty procedures when the targeted occlusion is hardened or calcified. It is believed typical angioplasty balloons, alone, may not be able to expand certain of these hardened lesions. Thus, angioplasty balloons equipped with cutting elements having cutting edges have been developed to attempt to enhance angioplasty treatments. Existing cutting elements tend to be fairly rigid. The rigid structure of the cutting elements limits the flexibility of the balloon, thereby limiting the ability of the cutting element, and the balloon to which it is mounted, to navigate through a tortuous vasculature of a patient.

Accordingly, there is an ongoing need for improved cutting elements, such as cutting blades, and methods of mounting cutting elements onto an inflatable angioplasty balloon of an angioplasty balloon catheter which enhance the flexibility of the construct. Namely, it would be desirable to provide a cutting member for use with an angioplasty balloon that is more flexible for navigating tortuous anatomy and more closely conforms to the expansion characteristics of the balloon to which it may be mounted.

SUMMARY

The disclosure is directed to several alternative designs, materials and methods of manufacturing medical device structures and assemblies, and the use thereof.

Accordingly, one illustrative embodiment is a medical balloon catheter including a catheter shaft and an inflatable balloon secured to a distal portion of the catheter shaft. The medical balloon catheter also includes a cutting member having a cutting edge and a base portion. The base portion includes a plurality of slots formed along a length of the base portion of the cutting member. A mounting pad encases or encapsulates the base portion for securing the cutting member to the inflatable balloon. Each of the slots has a T-shape with a horizontal segment having a first end and a second end and a vertical segment intersecting the horizontal segment intermediate the first end and the second end. The vertical segment opens to a lower surface of the cutting member. Each of the first end and the second end of the horizontal segment extends toward and is closer to the lower surface of the cutting member than an intermediate portion of the horizontal segment.

Another illustrative embodiment is a medical balloon catheter including a catheter shaft and an inflatable balloon secured to a distal portion of the catheter shaft. The medical balloon catheter also includes a cutting member mounted on the inflatable balloon. The cutting member has an undulating pattern including a plurality of peaks alternating with a plurality of valleys, with each peak located further from the balloon than each valley. The cutting member includes upper surface portions converging at the valleys and lower surface portions converging at the peaks. The upper surface portions converge to enlarged relief openings at the valleys and/or the lower surface portions converge to enlarged relief openings at the peaks. The relief openings are configured to reduce strain concentrations on the cutting member.

Yet another illustrative embodiment is a cutting balloon catheter including a balloon mounted on a distal portion of a catheter shaft. The cutting balloon catheter also includes a cutting member mounted on an exterior surface of the balloon. The cutting member has a length from a first end of the cutting member to a second end of the cutting member, and includes at least one discrete region of enhanced flexibility at a location along the length of the cutting member connecting a first portion of the cutting member to a second portion of the cutting member. The discrete region of enhanced flexibility permits the first portion of the cutting member to flex relative to the second portion of the cutting member without fracturing the first portion from the second portion.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIG. 4 is a plan view of an exemplary cutting member having a plurality of slots along the base of the cutting member;

FIG. 5 is a plan view of an exemplary cutting member having alternating peaks and valleys;

FIG. 5A is a plan view of an alternative configuration of the exemplary cutting member of FIG. 5;

Figure 1:
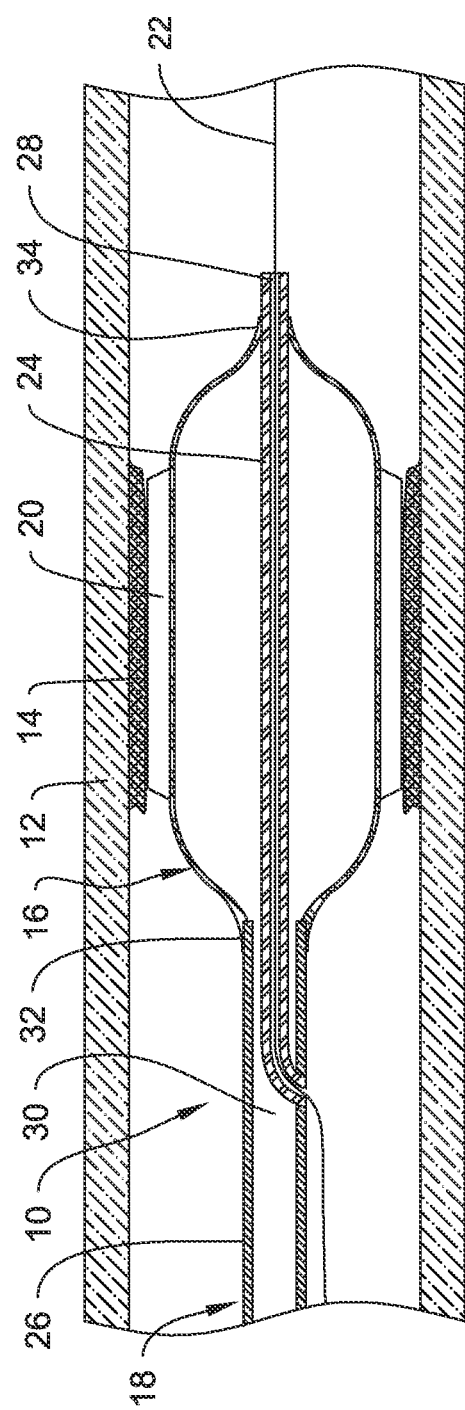
FIG. 1 is partial cross-sectional view of an exemplary cutting balloon catheter disposed in a blood vessel.

While the aspects of the disclosure amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 is a partial cross-sectional side view of an example catheter 10 disposed in a blood vessel 12 and positioned adjacent an intravascular lesion 14. The catheter 10 may include a balloon 16 coupled to a catheter shaft 18. One or more cutting members or blades 20 may be mounted on the balloon 16. In general, the catheter 10 may be advanced over a guidewire 22, through the vasculature, to a target area. Once positioned at the target location in the vasculature, the balloon 16 can be inflated to exert a radially outward force on the lesion 14, as the cutting members 20 engage the lesion 14. Thus, the cutting members 20 may cut or score the lesion 14 to facilitate enlarging the lumen proximate the lesion 14. The target area may be within any suitable peripheral or cardiac vessel lumen location.

The cutting members 20 may vary in number, position, and arrangement about the balloon 16. For example, the catheter 10 may include one, two, three, four, five, six, or more cutting members 20 that are disposed at any position along the balloon 16 and in a regular, irregular, or any other suitable pattern. For example, in some embodiments the balloon 16 may include a plurality of cutting members 20 longitudinally arranged symmetrically around the circumference of the balloon 16.

The cutting members 20 may be made from any suitable material such as a metal, metal alloy, polymer, metal-polymer composite, and the like, or any other suitable material. For example, cutting members 20 may be made from stainless steel, titanium, nickel-titanium alloys, tantalum, iron-cobalt-nickel alloys, or other metallic materials in some instances.

The balloon 16 may be made from typical angioplasty balloon materials including polymers such as polyethylene terephthalate (PET), polytetrafluoroethylene (PTFE), ethylene tetrafluoroethylene (ETFE), polybutylene terephthalate (PBT), polyurethane, polyvinylchloride (PVC), polyetherester, polyester, polyamide, elastomeric polyamides, polyether block amide (PEBA), as well as other suitable materials, or mixtures, combinations, copolymers thereof, polymer/metal composites, and the like. In some instances, the balloon 16 may include a single layer of material, whereas in other instances the balloon 16 may be of a multi-layer construction, including a plurality of layers of materials. For instance, the balloon 16 may be formed as a co-extrusion or tri-layer extrusion in some instances.

The balloon 16 may be configured so that the balloon 16 includes one or more "wings" or wing-shaped regions when the balloon 16 is deflated. In some instances, the wings may be configured so that the cutting members 20 can be positioned at the inward-most positions of the deflated balloon 16, with the wings of the balloon folds positioned between adjacent cutting members 20. This arrangement may reduce the exposure of the cutting members 20 to the blood vessel during delivery of the balloon 16 to the lesion 14.

The shaft 18 may be a catheter shaft, similar to typical catheter shafts. For example, the catheter shaft 18 may include an outer tubular member 26 and an inner tubular member 24 extending through at least a portion of the outer tubular member 26. Tubular members 24/26 may be manufactured from a number of different materials. For example, tubular members 24/26 may be made of metals, metal alloys, polymers, metal-polymer composites or any other suitable materials.

Tubular members 24/26 may be arranged in any appropriate way. For example, in some embodiments the inner tubular member 24 can be disposed coaxially within the outer tubular member 26. According to these embodiments, the inner and outer tubular members 24/26 may or may not be secured to one another along the general longitudinal axis of the catheter shaft 18. Alternatively, the inner tubular member 24 may follow the inner wall or otherwise be disposed adjacent the inner wall of the outer tubular member 26. In other embodiments, the tubular members 24/26 may be arranged in another desired fashion.

The inner tubular member 24 may include an inner lumen 28. In at least some embodiments, the inner lumen 28 is a guidewire lumen for receiving the guidewire 22 therethrough. Accordingly, the catheter 10 can be advanced over the guidewire 22 to the desired location. The guidewire lumen 28 may extend along essentially the entire length of the catheter shaft 18 such that catheter 10 resembles traditional "over-the-wire" catheters. Alternatively, the guidewire lumen 28 may extend along only a portion of the catheter shaft 18 such that the catheter 10 resembles "single-operator-exchange" or "rapid-exchange" catheters.

The catheter shaft 18 may also include an inflation lumen 30 that may be used, for example, to transport inflation media to and from the balloon 16 to selectively inflate and/or deflate the balloon 16. The location and position of the inflation lumen 30 may vary, depending on the configuration of the tubular members 24/26. For example, when the outer tubular member 26 surrounds the inner tubular member 24, the inflation lumen 30 may be defined within the space between the tubular members 24/26. In embodiments in which the outer tubular member 26 is disposed alongside the inner tubular member 24, then the inflation lumen 30 may be the lumen of the outer tubular member 26.

The balloon 16 may be coupled to the catheter shaft 18 in any of a number of suitable ways. For example, the balloon 16 may be adhesively or thermally bonded to the catheter shaft 18. In some embodiments, a proximal waist 32 of the balloon 16 may be bonded to the catheter shaft 18, for example, bonded to the distal end of the outer tubular member 26, and a distal waist 34 of the balloon 16 may be bonded to the catheter shaft 18, for example, bonded to the distal end of the inner tubular member 24. The exact bonding positions, however, may vary.

Figure 2:
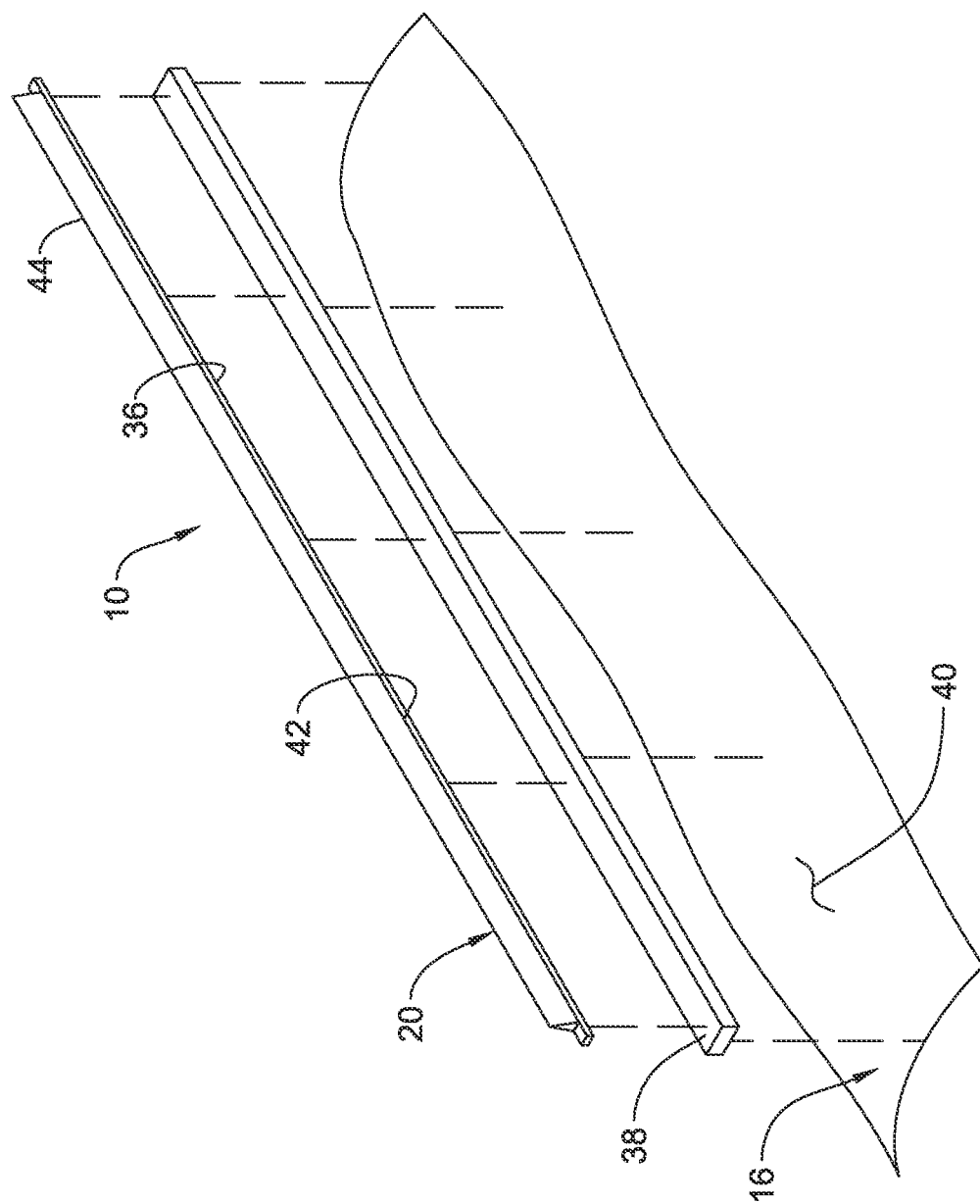
FIG. 2 is a partial perspective view of a cutting element and mounting pad for mounting the cutting element to a balloon.

Referring to FIG. 2, the cutting members 20 may include a base portion 42 and a cutting edge 44 opposite the base portion 42 extending radially outward from the balloon 16. The cutting members 20 may be secured to the outer surface 40 of the balloon 16 by encasing or embedding the base portion 42 of the cutting member 20 in a mounting pad 38 formed of a polymeric adhesive material, and adhesively bonding or otherwise securing the mounting pad 38, with the base portion 42 of the cutting member 20 embedded therein, to the outer surface 40 of the balloon 16. The base portion 42 of the cutting member 20 may be embedded to any desired depth within the mounting pad 38 such that the lower surface 36 of the cutting member 20 is located radially inward of the upper surface of the mounting pad 38.

Figure 3A:
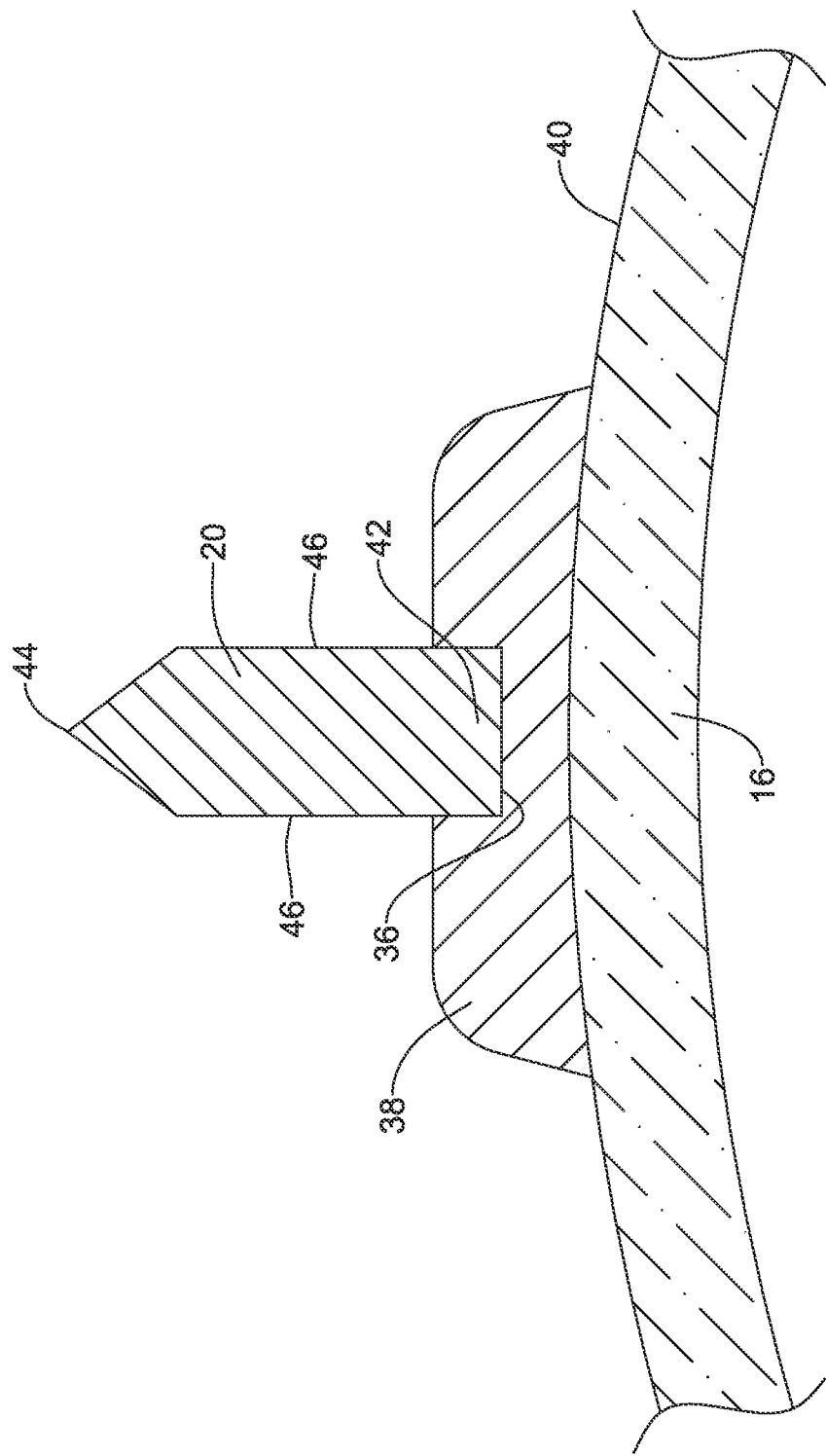
FIG. 3A is a cross-sectional view of an exemplary cutting element mounted to a balloon with a mounting pad.
Figure 3B:
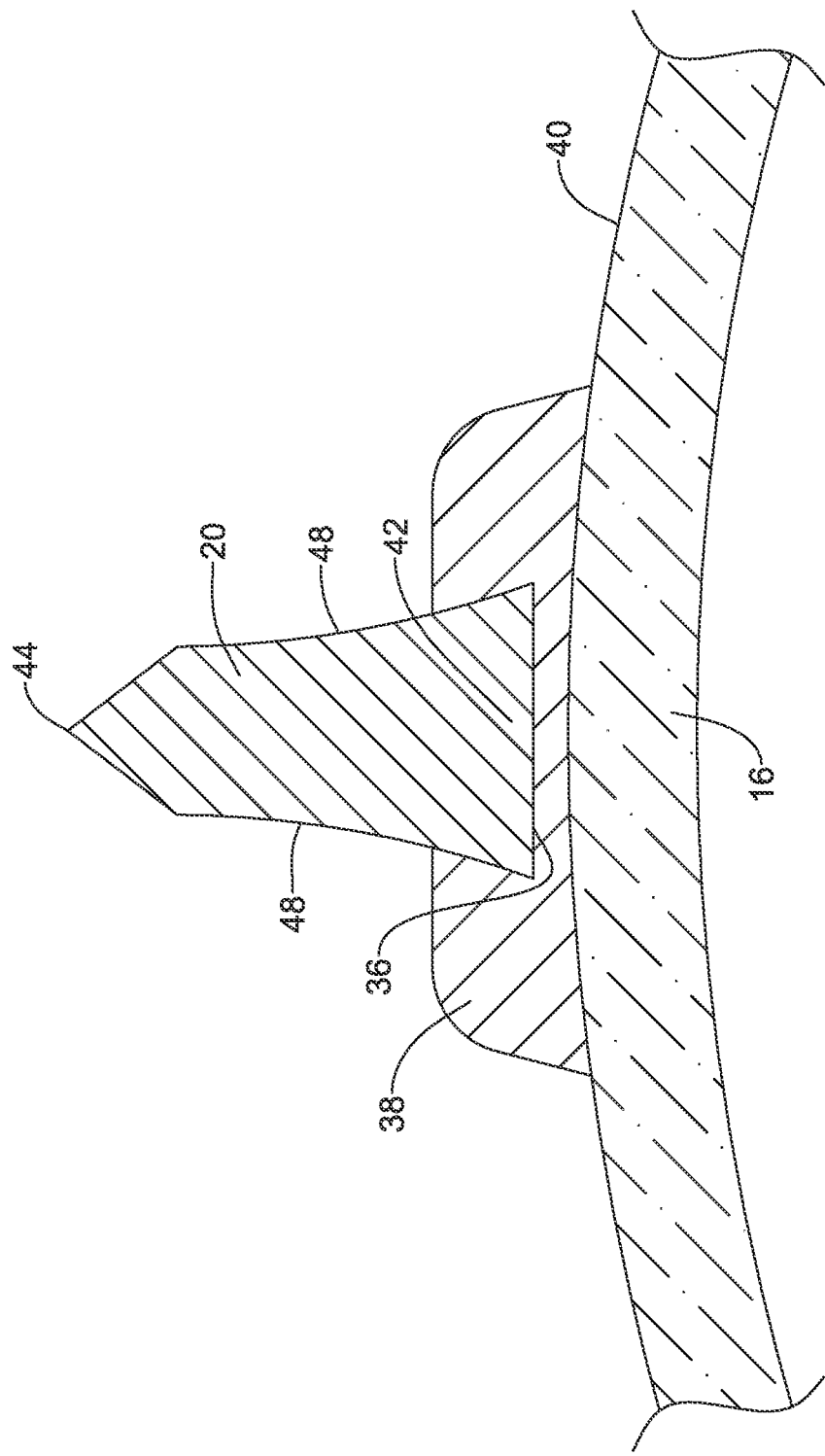
FIG. 3B is a cross-sectional view of another exemplary cutting element mounted to a balloon with a mounting pad.

Accordingly, FIGS. 3A and 3B illustrate exemplary embodiments of a cutting member 20 mounted to the balloon 16 with a mounting pad 38. As shown in FIG. 3A, the cutting member 20 may include generally parallel side surfaces 46 extending from the lower surface 36. The mounting pad 38 may surround and contact a portion of the side surfaces 46 to embed the base portion 42 in the mounting pad 38. In some instances, the cutting member 20 may be embedded in the mounting pad 38 such that a portion of the mounting pad 38 may be located between the lower surface 36 of the cutting member 20 and the outer surface 40 of the balloon 16.

In another embodiment, shown in FIG. 3B, the cutting member 20 may include flared side surfaces 48 in which the base portion 42 widens toward the lower surface 36. Similar to the embodiment shown in FIG. 3A, the mounting pad 38 may surround and contact a portion of the side surfaces 48 to embed the base portion 42 in the mounting pad 38. In some instances, the cutting member 20 may be embedded in the mounting pad 38 such that a portion of the mounting pad 38 may be located between the lower surface 36 of the cutting member 20 and the outer surface 40 of the balloon 16. The configuration of the flared side surfaces 48 may help lock the cutting member 20 in the mounting pad 38. Namely, the widened portion of the base portion 42 may be interlocked into the mounting pad 38 to prevent the cutting member 20 from passing through the portion of the mounting pad 38 adjacent the narrowed portion of the base portion 42, and thus preventing the cutting member 20 from lifting out of the mounting pad 38.

While FIGS. 1, 2 and 3A-3B illustrate a cutting member 20 generally, FIGS. 4-12 illustrate several embodiments of cutting members having notable features. Any of the cutting members described herein, may be mounted to a balloon 16 in a similar fashion as described above regarding the cutting member 20. It is understood that any of the features illustrated in one of the described embodiments, may be incorporated instead of or in addition to one or more features of another illustrated embodiment, and one or more features of any illustrated embodiment may be combined together in constructing a cutting element with desired characteristics.

FIG. 4 illustrates an exemplary cutting member 120 having a cutting edge 144 and a base portion 142. The base portion 142 may include a plurality of slots 150 alternating with a plurality of tabs 160. The slots 150 and tabs 160 may facilitate mechanical interlocking of the base portion 142 in the mounting pad 38 by permitting material of the mounting pad 38 to flow into or occupy, and interlock with the tabs 160. The shape of the slots 150 and tabs 160 may deter the base portion 142 from lifting out of or being removed from the mounting pad 38 once encapsulated therein. The slots 150 may have a T-shape with a horizontal segment 154 having a first end and a second end and a vertical segment 152 intersecting the horizontal segment 154 intermediate the first end and the second end of the horizontal segment 154. The vertical segment 152 may open out to the lower surface 136 of the cutting member 120. In some instances, the T-shaped slots 150 may be considered "mushroom" T-slots (e.g., end portions of the horizontal segment 154 of the slots 150 rolled downward relative to the intermediate portion of the horizontal segment 154), or T-slots having serifs 156 (e.g., end portions of the horizontal segment 154 of the slots 150 extending at an angle non-parallel to the intermediate portion of the horizontal segment 154, such as angling at an oblique or perpendicular angle to the intermediate portion. Accordingly, the T-shaped slots 150 may be configured such that each of the first end and the second end of the horizontal segment 154 extends toward and is closer to the lower surface 136 of the cutting member 120 than an intermediate portion of the horizontal segment 154. In some instances, the intermediate portion of the horizontal segment 154 may extend parallel to the lower surface 136 of the cutting member 120, and the serifs 156 may extend generally perpendicular to the intermediate portion of the horizontal segment 154 or at an oblique angle to the intermediate portion of the horizontal segment 154.

The base portion 142 of the cutting member 120 may be embedded or encapsulated in the mounting pad 38 when secured to a balloon 16. As a consequence of forming the serifs 156 formed at the opposing ends of the horizontal segment 154 of the T-shaped slots 150 a bump or lip of material 155 (e.g., a protuberance) of the tabs 160 of the cutting member 120 may be located between the serifs 156 and the vertical segment 152 which extends toward the cutting edge 144 above a lower extent of the serifs 156). The bump or lip of material 155 may be configured to interlock with the mounting pad 38 surrounding the bump or lip of material 155 to lock the base portion 142 of the cutting member 120 in the mounting pad 38. For example, material of the mounting pad 38 flowing into and occupying the serifs 156 of the T-shaped slots 150 may interlock with the bump or lip of material 155 to prevent the tabs 160 of the base portion 142 from lifting out of the mounting pad 38.

FIG. 5 illustrates another embodiment of a cutting member 220 formed of a strut 250 having an undulating pattern including a plurality of peaks 260 alternating with a plurality of valleys 262 in a cyclic pattern, with each peak 260 located further from the balloon 16 than each valley 262, and thus each valley 262 located closer to the balloon 16 than each peak 260. The strut 250 may include upper surface portions 266a, 266b and lower surface portions 268a, 268b opposite the upper surface portions 266a, 266b. The upper surface portions 266a, 266b converge at the valleys 262, and the lower surface portions 268a, 268b converge at the peaks 260. In some instances, the upper surface portions 266a, 266b may converge to enlarged relief openings 264 at the valleys 262 and/or the lower surface portions 268a, 268b may converge to enlarged relief openings 264 at the peaks 260. The strut 250 may be configured to flex at the peaks 260 and/or valleys 262 to impart flexibility in the cutting member 220. The relief openings 264 may be configured to reduce strain concentrations on the strut 250 of the cutting member 220 at the peaks 260 and/or valleys 262 when the strut 250 flexes at the peaks 260 and/or valleys 262.

Furthermore, the base portion 242 of the cutting member 220 may include an enlarged base member 270 (e.g., a foot) at each valley 262. Adjacent base members 270 may be spaced away from each other by a gap 272. The base members 270 may define a discontinuous lower surface 236 of the cutting member 220, allowing greater flexibility of the cutting member 220.

The base members 270 may be encased in the mounting pad 38 to secure the cutting member 220 to the inflatable balloon 16. When mounted in the mounting pad 38, the peaks 260 may extend above the mounting pad 38. In some embodiments, the valleys 262 may be embedded or encased in the mounting pad 38 with the base members 270, whereas in other embodiments the valleys 262 may remain above the mounting pad 38 while the base members 270 are embedded or encased in the mounting pad 38. In some instances, the enlarged relief openings 264 at the valleys 262 are embedded in the mounting pad 38 and the enlarged relief openings 264 at the peaks 260 may be exposed from the mounting pad 38. In other embodiments, the enlarged relief openings 264 at the valleys 262 may be either encased in the mounting pad 38 or exposed from the mounting pad 38.

FIG. 5A illustrates an alternative configuration of the cutting member 220 in which the peaks 260, are flattened peaks including a elongated longitudinal segment 280 extending between angled portions of the strut 250. In some instances the elongated longitudinal segment 280, or flat upper portion, may extend generally parallel to the longitudinal axis of the cutting member 220. The elongated longitudinal segment 280 may be of any desired length, and in some instances may include a cutting edge for engagement with tissue. Such an embodiment may provide additional length of contact of the cutting member 220 with tissue. The struts 250 may include enlarged relief openings 264 at each end of the elongated longitudinal segment 280 where the elongated longitudinal segment 280 is joined to the angled portions of the struts 250 extending from the base members 270 at the valleys 262 to the peaks 260.

Figure 6:
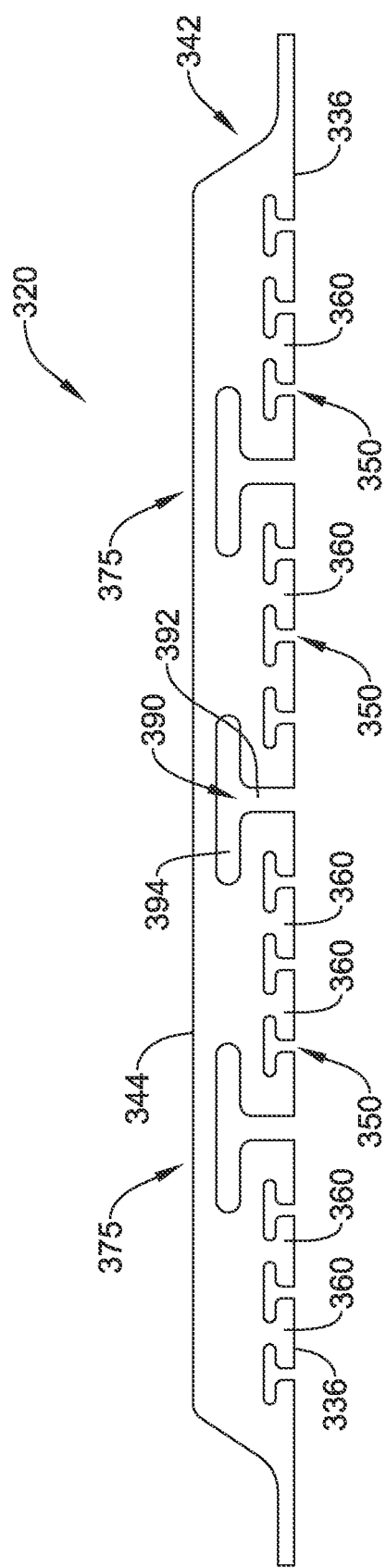
FIG. 6 is a plan view of an exemplary cutting member having one or more larger T-slots intermingled with a plurality of smaller T-slots along the base of the cutting member.

FIG. 6 illustrates another exemplary embodiment of a cutting member 320 having a cutting edge 344 and a base portion 342. The base portion 342 may include a plurality of slots 350 alternating with a plurality of tabs 360. The slots 350 may have a T-shape with a horizontal segment having a first end and a second end and a vertical segment intersecting the horizontal segment intermediate the first end and the second end of the horizontal segment. The vertical segment may open out to the lower surface 336 of the cutting member 320. Correspondingly, the tabs 360 may have an inverted T-shape.

The cutting member 320, which may have a length from a first end of the cutting member 320 to a second end of the cutting member 320, may include at least one discrete region of enhanced flexibility 375 at a location along the length of the cutting member 320 connecting a first portion of the cutting member 320 to a second portion of the cutting member 320. The cutting member 320 is illustrated as including a plurality of discrete regions of enhanced flexibility 375. The discrete regions of enhanced flexibility 375 may permit the first portion of the cutting member 320 to flex relative to the second portion of the cutting member 320 without fracturing the first portion from the second portion under normal usage.

For example, the discrete regions of enhanced flexibility 375 may include a large T-shaped slot 390 larger than each of the small T-shaped slots 350. The large T-shaped slots 390 may include a horizontal segment 394 having a first end and a second end and a vertical segment 392 intersecting the horizontal segment 394 intermediate the first end and the second end of the horizontal segment 394. The vertical segment 392 may open out to the lower surface 336 of the cutting member 320 between adjacent small T-shaped slots 350. The horizontal segment 394 may be located above the horizontal segments of the small T-shaped slots 350.

In using the terms "small" and "large" to describe the T-shaped slots 350, 390, these terms are used in their usual sense to describe the size of the small T-shaped slots 350 relative to the large T-shaped slots 390. For example, the small T-shaped slots 350 may have a height in the range of about 0.002 inches to about 0.006 inches and a width in the range of about 0.007 inches to about 0.015 inches, in some instances. The large T-shaped slots 390 may have a height in the range of about 0.007 inches to about 0.010 inches and a width in the range of about 0.020 inches to about 0.035 inches, in some instances.

The base portion 342, including the small T-shaped slots 350 and tabs 360, may be encased or embedded in the mounting pad 38 to secure the cutting member 320 to the inflatable balloon 16, while at least an upper portion of the large T-shaped slots 390 may extend above the mounting pad 38. The large T-shaped slots 390 may provide the cutting member 320 with increased flexibility allowing a first portion of the cutting member 320 located to one side of the large T-shaped slot 390 to bend or flex relative to a second portion of the cutting member 320 located to an opposite side of the large T-shaped slot 390.

Figure 7:
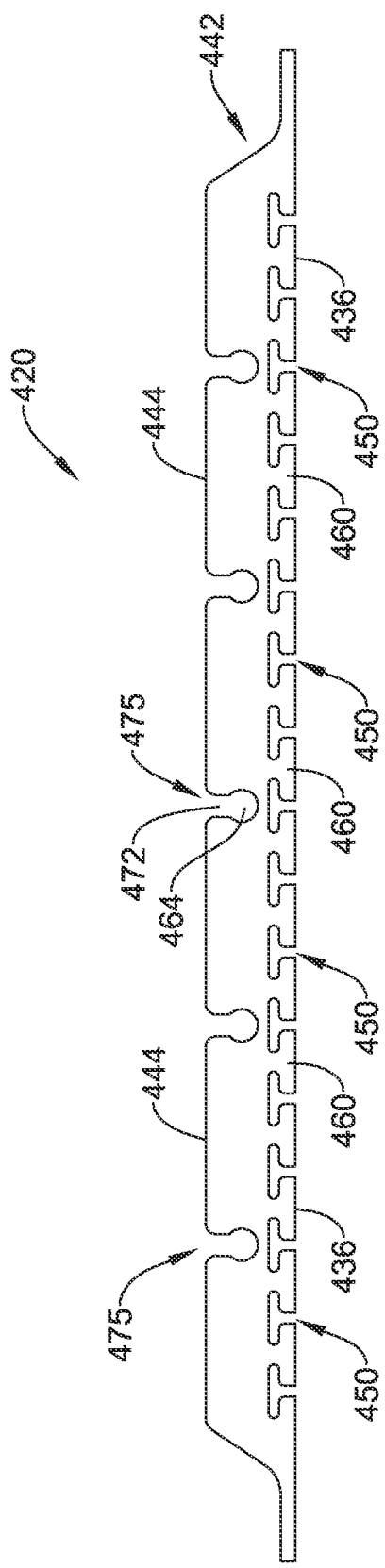
FIG. 7 is a plan view of an exemplary cutting member having one or more recesses or notches along the cutting edge.

FIG. 7 illustrates another exemplary embodiment of a cutting member 420 having a cutting edge 444 and a base portion 442. The base portion 442 may include a plurality of slots 450 alternating with a plurality of tabs 460. The slots 450 may have a T-shape with a horizontal segment having a first end and a second end and a vertical segment intersecting the horizontal segment intermediate the first end and the second end of the horizontal segment. The vertical segment may open out to the lower surface 436 of the cutting member 420. Correspondingly, the tabs 460 may have an inverted T-shape. The base portion 442, including the T-shaped slots 450 and tabs 460, may be encased or embedded in the mounting pad 38 to secure the cutting member 420 to the inflatable balloon 16.

The cutting member 420, which may have a length from a first end of the cutting member 420 to a second end of the cutting member 420, may include at least one discrete region of enhanced flexibility 475 at a location along the length of the cutting member 420 connecting a first portion of the cutting member 420 to a second portion of the cutting member 420. The cutting member 420 is illustrated as including a plurality of discrete regions of enhanced flexibility 475. The discrete regions of enhanced flexibility 475 may permit the first portion of the cutting member 420 to flex relative to the second portion of the cutting member 420 without fracturing the first portion from the second portion under normal usage.

For example, the discrete regions of enhanced flexibility 475 may include a notch or slot 472 extending from the cutting edge 444 of the cutting member 420 toward the base portion 442 of the cutting member 420. The notches 472 may divide the cutting member 420 into a plurality of interconnected segments each having a discontinuous portion of the cutting edge 444. The notch 472, which opens out to the cutting edge 444, includes a first open end proximate the cutting edge 444 and a second closed end proximate the base portion 442. In some instances, the second closed end of the notches 472 may include an enlarged relief opening 464 configured to reduce strain concentrations on the cutting member 420 when flexed at the notches 472. For example, the enlarged relief opening 464 may have a width greater than a width of the notch 472 above the enlarged relief opening 464. For instance, the enlarged relief opening 464 may have a width greater than the width of the remainder of the notch 472 extending between the enlarged relief opening 464 and the cutting edge 444, or at least the portion of the notch 472 immediately adjacent to the enlarged relief opening 464.

Figure 8:
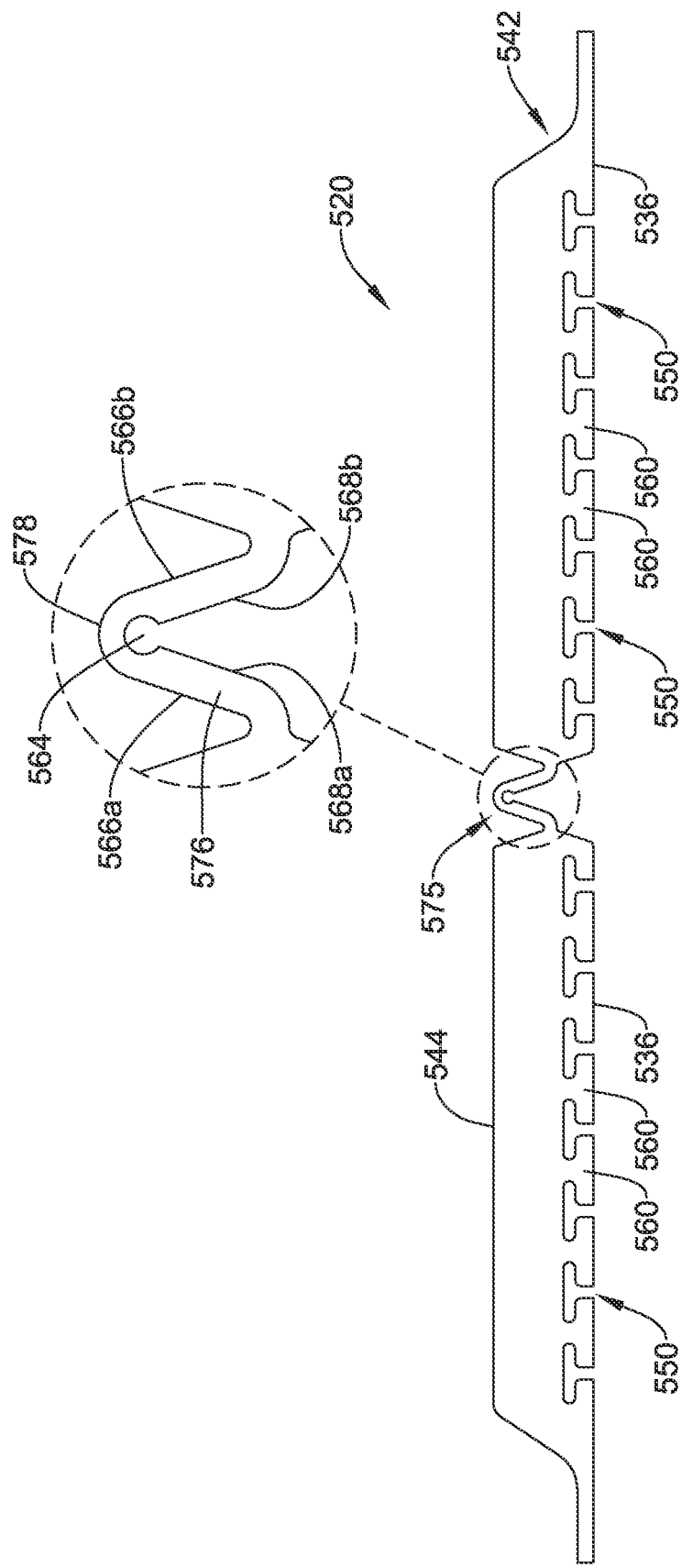
FIG. 8 is a plan view of an exemplary cutting member having one or more flexible struts or links.

FIG. 8 illustrates another exemplary embodiment of a cutting member 520 having a cutting edge 544 and a base portion 542. The base portion 542 may include a plurality of slots 550 alternating with a plurality of tabs 560. The slots 550 may have a T-shape with a horizontal segment having a first end and a second end and a vertical segment intersecting the horizontal segment intermediate the first end and the second end of the horizontal segment. The vertical segment may open out to the lower surface 536 of the cutting member 520. Correspondingly, the tabs 560 may have an inverted T-shape. The base portion 542, including the T-shaped slots 550 and tabs 560, may be encased or embedded in the mounting pad 38 to secure the cutting member 520 to the inflatable balloon 16.

The cutting member 520, which may have a length from a first end of the cutting member 520 to a second end of the cutting member 520, may include at least one discrete region of enhanced flexibility 575 at a location along the length of the cutting member 520 connecting a first portion of the cutting member 520 to a second portion of the cutting member 520. The discrete region of enhanced flexibility 575 may permit the first portion of the cutting member 520 to flex relative to the second portion of the cutting member 520 without fracturing the first portion from the second portion under normal usage.

For example, the discrete region of enhanced flexibility 575 may include a strut 576, such as a V-shaped strut or living hinge, connecting the first portion of the cutting member 520 to the second portion of the cutting member 520. In some embodiments, the strut 576 may divide the cutting member 520 into a plurality of interconnected segments each having a discontinuous portion of the cutting edge 544. In some instances, the V-shaped strut 576 may include first and second legs converging toward the cutting edge 544 of the cutting member 520. However, in other instances, the first and second legs of the V-shaped strut 576 may converge toward the lower surface 536 of the base portion 542 of the cutting member 520.

The strut 576 may include upper surface portions 566a, 566b and lower surface portions 568a, 568b opposite the upper surface portions 566a, 566b. The upper surface portions 566a, 566b and lower surface portions 568a, 568b may converge at a tip 578. In some instances, in which the V-shaped strut 576 is pointed toward the cutting edge 544, the lower surface portions 568a, 568b may converge to an enlarged relief opening 564 at the tip 578. In instances in which the V-shaped strut 576 is pointed toward the lower surface 536 of the base portion 542, the upper surface portions 566a, 566b may converge to an enlarged relief opening 564. The strut 576 may be configured to flex to impart flexibility in the cutting member 520. The relief opening 564 may be configured to reduce strain concentrations on the strut 576 of the cutting member 520 at the tip 578 when the strut 576 flexes.

Figure 9:
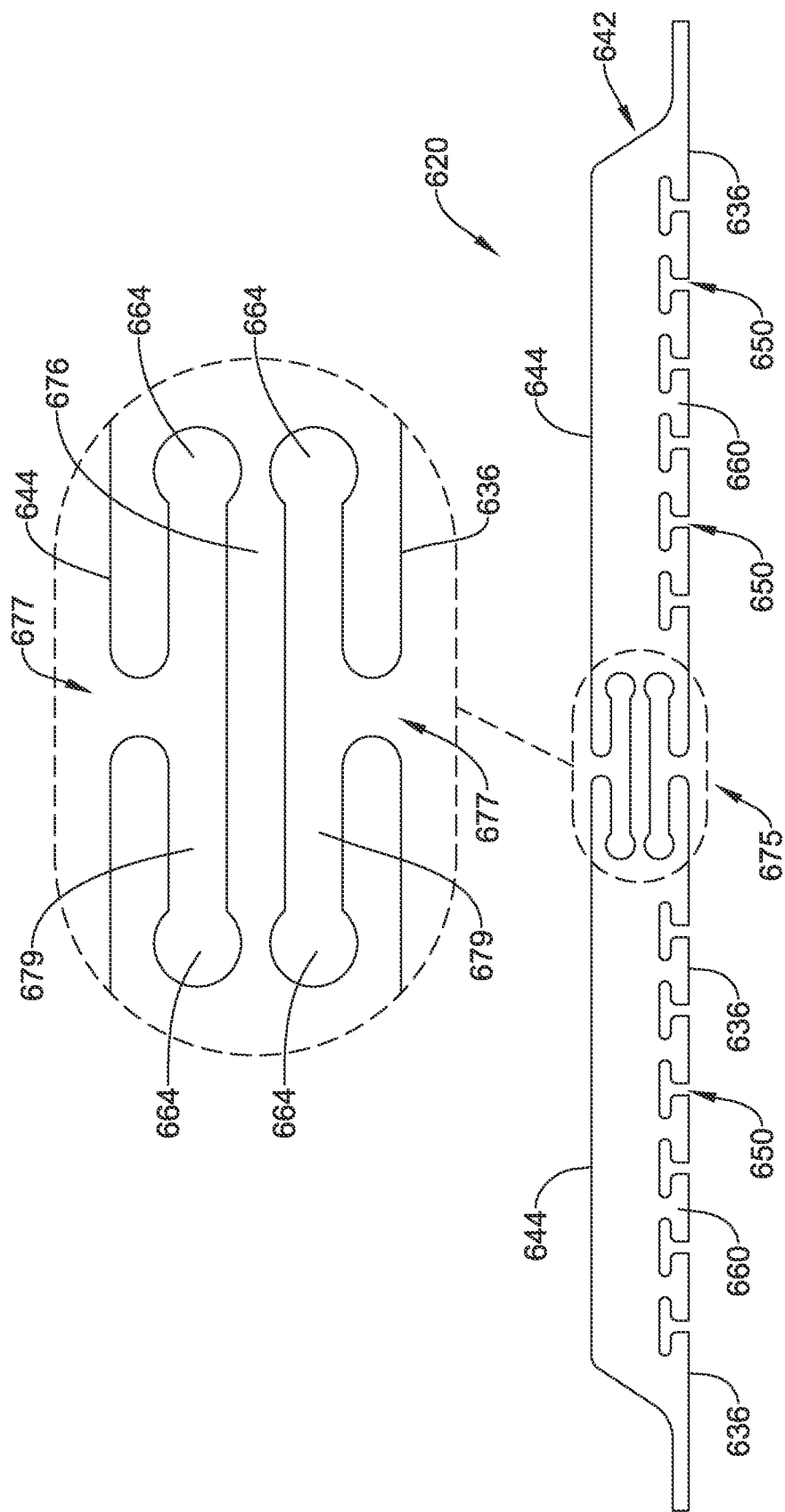
FIG. 9 is a plan view of an exemplary cutting member having one or more flexible struts or links.

FIG. 9 illustrates another exemplary embodiment of a cutting member 620 having a cutting edge 644 and a base portion 642. The base portion 642 may include a plurality of slots 650 alternating with a plurality of tabs 660. The slots 650 may have a T-shape with a horizontal segment having a first end and a second end and a vertical segment intersecting the horizontal segment intermediate the first end and the second end of the horizontal segment. The vertical segment may open out to the lower surface 636 of the cutting member 620. Correspondingly, the tabs 660 may have an inverted T-shape. The base portion 642, including the T-shaped slots 650 and tabs 660, may be encased or embedded in the mounting pad 38 to secure the cutting member 620 to the inflatable balloon 16.

The cutting member 620, which may have a length from a first end of the cutting member 620 to a second end of the cutting member 620, may include at least one discrete region of enhanced flexibility 675 at a location along the length of the cutting member 620 connecting a first portion of the cutting member 620 to a second portion of the cutting member 620. The discrete region of enhanced flexibility 675 may permit the first portion of the cutting member 620 to flex relative to the second portion of the cutting member 620 without fracturing the first portion from the second portion under normal usage.

For example, the discrete region of enhanced flexibility 675 may include a strut 676, such as a horizontal link, connecting the first portion of the cutting member 620 to the second portion of the cutting member 620. In some embodiments, the strut 676 may divide the cutting member 620 into a plurality of interconnected segments each having a discontinuous portion of the cutting edge 644. In some instances, the strut 676 may extend generally horizontally or axially from a first root end of the strut 676 connected to the first portion to a second root end of the strut 676 connected to the second portion along a longitudinal axis of the cutting member and parallel to the lower surface 636 of the base portion 642.

The discrete region of enhanced flexibility 675 may include elongate slots 679 formed in the cutting member 620 above and below the strut 676, thereby defining the strut 676 therebetween. In some instances, the elongate slots 679 may have a long axis generally parallel to the strut 676, and thus generally parallel to the cutting edge 644 and/or the lower surface 636.

In some instances, the ends of the slots 679, proximate the root ends of the strut 676 (i.e., where the strut 676 connects to the first and second portions of the cutting member 620), may include an enlarged relief opening 664 configured to reduce strain concentrations on the cutting member 620 when flexed at the discrete region of enhanced flexibility 675. For example, the enlarged relief openings 664 may have a width greater than a width of the slots 679 extending between the enlarged relief openings 664. For instance, the enlarged relief openings 664 may have a width greater than the width of the remainder of the slot 679 extending between the enlarged relief openings 664, or at least the portion of the slot 679 immediately adjacent to the enlarged relief openings 664.

The cutting member 620 may additionally include a gap 677 in the cutting edge 644 opening into the slot 679 above the strut 676 and/or a gap 677 in the base portion 642 opening into the slot 679 below the strut 676 from the lower surface 636. The gaps 677 may have a width less than the length of the slots 679 and the strut 676. The gaps 677 may provide further flexibility in the cutting member 620 at the discrete region of enhanced flexibility 675.

Figure 10:
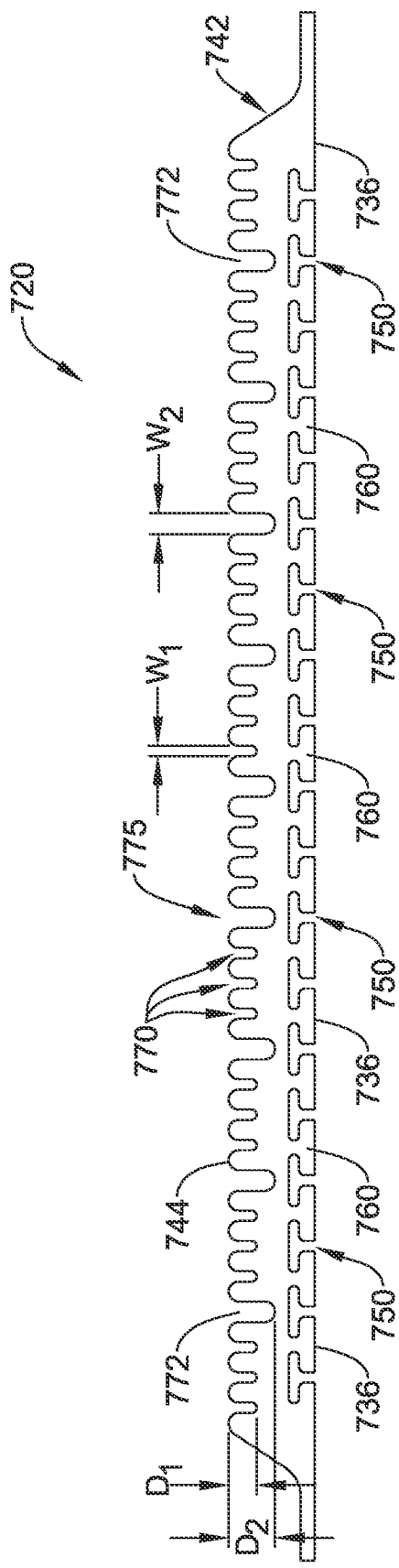
FIG. 10 is a plan view of an exemplary cutting member having a serrated cutting edge including serrations of various depths.

FIG. 10 illustrates another exemplary embodiment of a cutting member 720 having a serrated cutting edge 744 and a base portion 742. The base portion 742 may include a plurality of slots 750 alternating with a plurality of tabs 760. The slots 750 may have a T-shape with a horizontal segment having a first end and a second end and a vertical segment intersecting the horizontal segment intermediate the first end and the second end of the horizontal segment. The vertical segment may open out to the lower surface 736 of the cutting member 720. Correspondingly, the tabs 760 may have an inverted T-shape. The base portion 742, including the T-shaped slots 750 and tabs 760, may be encased or embedded in the mounting pad 38 to secure the cutting member 720 to the inflatable balloon 16.

The cutting member 720, which may have a length from a first end of the cutting member 720 to a second end of the cutting member 720, may include at least one discrete region of enhanced flexibility 775 at a location along the length of the cutting member 720 connecting a first portion of the cutting member 720 to a second portion of the cutting member 720. The cutting member 720 is illustrated as including a plurality of discrete regions of enhanced flexibility 775. The discrete regions of enhanced flexibility 775 may permit the first portion of the cutting member 720 to flex relative to the second portion of the cutting member 720 without fracturing the first portion from the second portion under normal usage.

For example, the serrated cutting edge 744 may include a plurality of notches 770 extending from the cutting edge 744 toward the base portion 742 of the cutting member 720, and the discrete regions of enhanced flexibility 775 may include one of the plurality of notches 772 having a length greater than a length of a remainder of the plurality of notches 770. In other words, the notches 770 may have a depth $D_1$ from the upper extent of the cutting member 720, whereas the notches 772 may have a depth $D_2$ from the upper extent of the cutting member 720 greater than the depth $D_1$ of the notches 770. Furthermore, in some instances, the notches 770 may have a width $W_1$, measured in the axial direction, less than a width $W_2$ of the notches 772.

As shown in FIG. 10, the serrated cutting edge 744 may include a plurality of the smaller notches 770 between each pair of larger notches 772. For example, the serrated cutting edge 744 may include two, three, four, five, six, seven, eight or more small notches 770 between each pair of large notches 772. The large notches 772 extending toward the base portion 742, may provide increased flexibility to the cutting member 720

Figure 11:
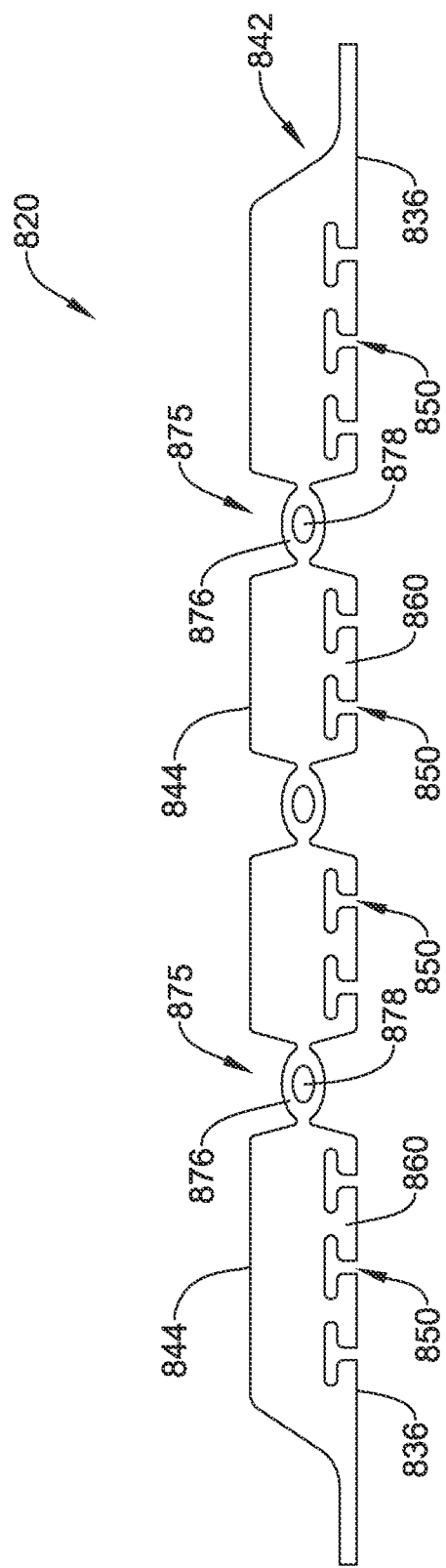
FIG. 11 is a plan view of an exemplary cutting member having one or more flexible struts or links.

FIG. 11 illustrates another exemplary embodiment of a cutting member 820 having a cutting edge 844 and a base portion 842. The base portion 842 may include a plurality of slots 850 alternating with a plurality of tabs 860. The slots 850 may have a T-shape with a horizontal segment having a first end and a second end and a vertical segment intersecting the horizontal segment intermediate the first end and the second end of the horizontal segment. The vertical segment may open out to the lower surface 836 of the cutting member 820. Correspondingly, the tabs 860 may have an inverted T-shape. The base portion 842, including the T-shaped slots 850 and tabs 860, may be encased or embedded in the mounting pad 38 to secure the cutting member 820 to the inflatable balloon 16.

The cutting member 820, which may have a length from a first end of the cutting member 820 to a second end of the cutting member 820, may include at least one discrete region of enhanced flexibility 875 at a location along the length of the cutting member 820 connecting a first portion of the cutting member 820 to a second portion of the cutting member 820. The cutting member 820 is illustrated as including a plurality of discrete regions of enhanced flexibility 875. The discrete regions of enhanced flexibility 875 may permit the first portion of the cutting member 820 to flex relative to the second portion of the cutting member 820 without fracturing the first portion from the second portion under normal usage.

For example, the discrete regions of enhanced flexibility 875 may include a bifurcated strut 876, having upper and lower portions with an opening 878 therebetween, connecting the first portion of the cutting member 820 to the second portion of the cutting member 820. In some embodiments, the strut 876 may divide the cutting member 820 into a plurality of interconnected segments each having a discontinuous portion of the cutting edge 844. In some instances, the strut 876 may be considered a "fish-eye" strut having the opening 878 extending through a central portion of the strut 876 with material of the strut 876 surrounding the opening 878. In some instances, the opening 878 through the strut 876 may be intermediate the root ends of the strut 876 (i.e., where the strut 876 connects to the first and second portions of the cutting member 820).

Figure 12:
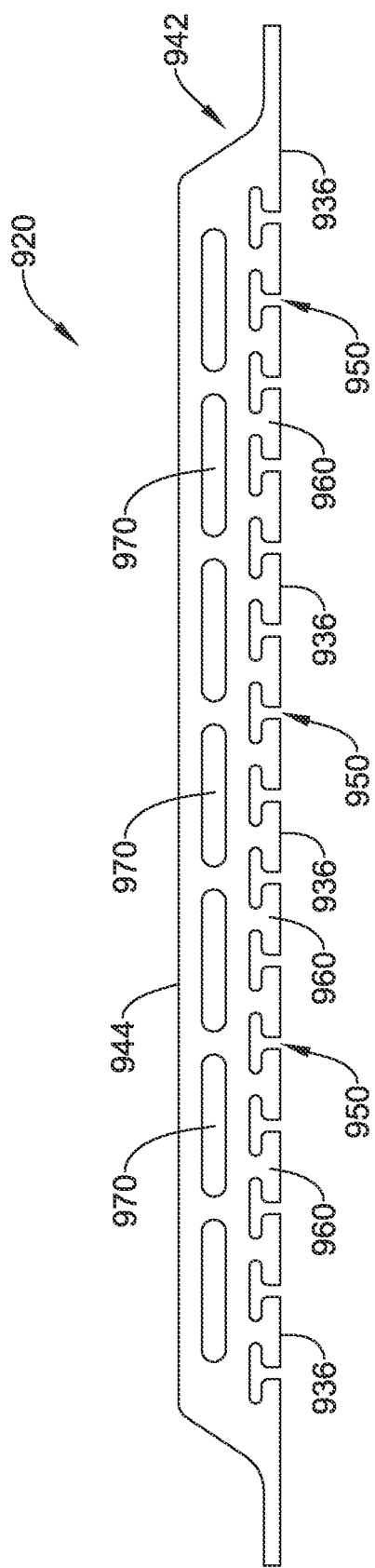
FIG. 12 is a plan view of an exemplary cutting member including a plurality of elongate cut-outs.

FIG. 12 illustrates another exemplary embodiment of a cutting member 920 having a cutting edge 944 and a base portion 942. The base portion 942 may include a plurality of slots 950 alternating with a plurality of tabs 960. The slots 950 may have a T-shape with a horizontal segment having a first end and a second end and a vertical segment intersecting the horizontal segment intermediate the first end and the second end of the horizontal segment. The vertical segment may open out to the lower surface 936 of the cutting member 920. Correspondingly, the tabs 960 may have an inverted T-shape. The base portion 942, including the T-shaped slots 950 and tabs 960, may be encased or embedded in the mounting pad 38 to secure the cutting member 920 to the inflatable balloon 16.

The cutting member 920 may include a plurality of elongate slots 970 formed along the length of the cutting member 920. For example, the plurality of elongate slots 970 may be disposed generally longitudinally along the longitudinal axis of the cutting member 920. An axial row of the elongate slots 970 may be located within the cutting member 920 between the cutting edge 944 and the base portion 942. The elongate slots 970 may provide enhanced flexibility regions along the length of the cutting member 920, permitting a first portion of the cutting member 920 to flex relative to a second portion of the cutting member 920 without fracturing the first portion from the second portion under normal usage.

The above described features of the cutting members may permit the cutting members mounted to a balloon to be more flexible for navigating tortuous anatomy and more closely conform to the expansion characteristics of the balloon to which the cutting members may be mounted.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A medical balloon catheter comprising:
a catheter shaft;
an inflatable balloon secured to a distal portion of the catheter shaft;
a cutting member extending from a first end to a second end and having a first portion and a second portion, each portion including a cutting edge and a base portion;
a mounting pad for securing the base portion to the inflatable balloon;
wherein the first portion and the second portion of the cutting member are connected by at least one region of enhanced flexibility between the first end and the second end of the cutting member;
wherein each region of enhanced flexibility includes at least one vertical slot extending from the cutting edge;
wherein each one of the at least one vertical slot includes a first open end proximate the cutting edge and a second closed end proximate the base portion;
wherein the second closed end includes an enlarged region having a width larger than a width of a remainder of the at least one vertical slot; and
wherein the region of enhanced flexibility is configured to allow the first portion to flex relative to the second portion without fracturing the first portion from the second portion.

2. The medical balloon catheter of claim 1, wherein the at least one vertical slot extends toward the base portion.

3. The medical balloon catheter of claim 1, wherein the cutting edge of the first portion is discontinuous from the cutting edge of the second portion.

4. The medical balloon catheter of claim 3, wherein the base portion of the first portion is discontinuous from the base portion of the second portion.

5. The medical balloon catheter of claim 1, wherein the base portions of the first portion and the second portion include a plurality of slots formed along a length of the base portions.

6. The medical balloon catheter of claim 5, wherein each of the plurality of slots has a T-shape with a horizontal segment having a first end and a second end and a vertical segment intersecting the horizontal segment intermediate the first end and the second end, the vertical segment opening to a lower surface of the cutting member.

7. A medical balloon catheter comprising:
a catheter shaft;
an inflatable balloon secured to a distal portion of the catheter shaft; and
a cutting member mounted on the balloon, the cutting member including:
a first portion having a first cutting edge and a first base portion;
a second portion having a second cutting edge and a second base portion; and
at least one region of enhanced flexibility connecting the first portion and the second portion and configured to allow the first portion to flex relative to the second portion without fracturing the first portion from the second portion, wherein each region of enhanced flexibility includes a vertical slot extending radially from the cutting edges towards the base portions;
wherein the vertical slot includes a first open end between the first and second cutting edges and a second closed end proximate the first and second base portions;
wherein the second closed end includes an enlarged region having a width larger than a width of a remainder of the vertical slot.

8. The medical balloon catheter of claim 7, wherein the first and second base portions of the first and the second portions include a plurality of slots formed along a length of the first and second base portions.

9. A medical balloon catheter comprising:
a catheter shaft;
an inflatable balloon secured to a distal portion of the catheter shaft; and
a cutting member secured to the balloon, the cutting member having a first end and a second end and including:
a first portion that includes the first end, a first cutting edge, and a first base portion;
a second portion that includes the second end, a second cutting edge, and a second base portion; and
a region of enhanced flexibility connecting the first portion and the second portion and configured to allow the first portion to flex relative to the second portion without fracturing the first portion from the second portion, wherein the region of enhanced flexibility includes a vertical slot extending from the cutting edges towards the base portions;

wherein the vertical slot includes a first open end between the first and second cutting edges and a second closed end proximate the first and second base portions wherein the second closed end includes an enlarged region having a width larger than a width of a remainder of the vertical slot.

* * * * *